United States Patent [19]

Modrovich

[11] 4,310,625

[45] Jan. 12, 1982

[54] STABILIZED LIQUID ENZYME COMPOSITIONS FOR DIAGNOSTIC DETERMINATIONS

[76] Inventor: Ivan E. Modrovich, 591 Beverly Dr., Camarillo, Calif. 93010

[21] Appl. No.: 898,704

[22] Filed: Apr. 24, 1978

Related U.S. Application Data

[63] Continuation of Ser. No. 667,856, Mar. 17, 1976, abandoned.

[51] Int. Cl.³ .......................... C12Q 1/32; C12Q 1/50; C12Q 1/52; C12N 9/96
[52] U.S. Cl. ........................................ 435/15; 435/14; 435/16; 435/17; 435/26; 435/188; 435/190; 435/194
[58] Field of Search .............. 195/63, 68, 99, 163.5 R; 435/16, 26, 188, 190, 194, 14, 15, 17

[56] References Cited

U.S. PATENT DOCUMENTS

| | | | |
|---|---|---|---|
| 3,557,002 | 1/1971 | McCarty | 195/63 X |
| 3,627,688 | 12/1971 | McCarty et al. | 195/63 X |
| 3,764,478 | 10/1973 | Bergmeyer et al. | 195/99 |
| 3,819,528 | 6/1974 | Berry | 195/63 X |

OTHER PUBLICATIONS

George, et al. Stabilization of Lactate and Malete Dehydrogenase by Organic Solvents Biochim. Biophys. Acta. vol. 191, 1969 (pp. 466–468).

*Primary Examiner*—David M. Naff
*Attorney, Agent, or Firm*—Robert J. Schaap

[57] ABSTRACT

Labile enzymes for use in biological diagnostic determinations are stabilized for long terms by forming a solution of the enzyme in an aqueous media containing at least 20% organic solvent such as 30% aqueous propane diol in the presence of a small amount of polymer such as 0.1% gelatin and then diluting the media at least 20 times with water while maintaining the polymer concentration at least 0.01%. The resultant liquid enzyme composition can be stored for extended periods without loss of significant enzyme catalytic activity. Stability is further enhanced by including from 1 to 18% of salts and 0.1% bacteriastatic agents in the liquid enzyme composition. The liquid enzyme composition enzyme can further contain an enzyme substrate and buffer salts.

26 Claims, No Drawings

STABILIZED LIQUID ENZYME COMPOSITIONS FOR DIAGNOSTIC DETERMINATIONS

RELATED APPLICATION

This application is a continuation of application Ser. No. 667,856, filed Mar. 17, 1976, for STABILIZED LIQUID ENZYME REAGENT COMPOSITIONS (now abandoned).

BACKGROUND OF THE INVENTION

1. Field of the Invention

This invention relates to the stabilization of labile enzymes in liquid media.

2. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement stems from the fact that the exact nature of enzymes, as well as the mechanisms of their action, remain unknown for the most part. At present, the greatest limitation on the enzyme reagent manufacturer, by far, lies in the unstable characteristics of his products. Current methodologies require the use of numerous labile ingredients, and these ingredients are more likely to increase, rather than decrease, in number.

The present commercial state of the art used for stabilizing the reactive ability of enzymes is by locking them into a solid matrix either by freeze drying, dry blending such as used for tableting dried powders, primarily in the pharmaceutical diagnostic and related industries and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried controlled sera reference serum list the acceptable bottle to bottle variation of enzyme constituents at ±10% of the mean.

SUMMARY OF THE INVENTION

Labile enzymes are chemically modified according to the invention resulting in long term stability without affecting enzymatic reactivity in accordance with the invention. The invention provides reagents where quality control is assured throughout manufacturing, packaging, storage and use. The inconvenience of rigid package size is eliminated as is the high cost of packaging, freeze drying and reagent waste. Liquid enzyme systems provide application flexibility and separation of the ingredients is easily accomplished with negligible manufacturing cost providing the flexibility of triggering the desired reaction after all side reactions have been dissipated.

The stabilized enzymes of the invention have been assessed in studies which compared liquid enzyme reagents with fresh reagents. The studies show a 1:1 correlation between liquid and fresh reagents with comparable sensitivity and precision. Providing enzyme reagents in liquid form enhances the colorimetric applicability of present day NAD/NADH coupled methodologies primarily because the separation of ingredients is easily accomplished. Liquid reagents are especially advantageous where NADH consumption is the basis of measurement and the color reagent must be separated from NADH and the reaction main. In the ultraviolet mode, the liquid enzyme system offers better reagent homogeneity and packaging, as well as flexibility in usage, in contrast to the freeze dried or dry media preparations.

In diagnostic enzymology, the stabilization of enzyme reagents in a ready-to-use liquid media is a new and exciting approach to satisfy the needs of the clinical laboratory and the reliability demands of the regulatory authorities. The flexibility of liquid enzyme systems insures their applicability to automated instrumentation, as well as their convenience in manual testings.

Stabilization of labile enzymes is accomplished in accordance with the invention by dissolving lyophilized, dry enzymes in an aqueous enzyme base including at least 0.05% of polymer and at least 20% v/v of organic solvent. The solution is maintained at a temperature below the denaturing point suitably below 60° C. and in most cases below 40° C. for at least 30 minutes, usually 2 to 3 days. The solution is then diluted with water typically at least a 20 times and usually a 30 times dilution while adding further polymer to maintain a level in diluted stage of at least 0.05 weight %. When the solution containing 20% V/V of organic solvent is diluted at least 20 times, the percentage of the solvent is 1%, and when diluted at a 30 times dilution, the percentage of the solvent is 0.75%. However, the solvent may be present from 0.05% to 5% in the final composition. The diluted solution suitably at an enzyme concentration from 100 to 10,000 I.U. per liter may then be packaged in separate containers and sealed and is stored refrigerated at temperatures of 30° C. or less.

As used herein, and particularly in the claims, the term "bactericidal" is used in a generic sense and shall mean bactericidal and fungicidal agents.

The diluted solution may also contain substrate buffer and bacteriastatic agent and other components if necessary. If these other ingredients are added the diluted solution is mixed to obtain a single homogeneous substrate solution before dispensing into individual containers, sealing and storage.

Substrates are organic chemicals of known structure whose reactions or interactions are catalyzed by enzymes resulting in a change in the compound structure, atomic composition, or stereo chemical rotation, for example, lactic acid, L-aspartate or, alphaketoglutarate, L-alanine or the like.

In general, substrates are prone to microbiological degradation as they serve as food for bacteria, fungi and other microorganisms. Otherwise, these compounds remain stable in aqueous media at or near neutral pH typically from 4–10. Thus if the substrate is added to the enzyme composition the stabilizing media should also contain a buffer to control reaction pH such as an alkali metal acid phosphate and a bactericidal and/or fungicidal agents which do not chemically react with the substrate or inhibit the enzymatic reaction of the substrate. Typical examples are 0.01% to 0.3% sodium azide, benzoic acid, phenol, thymol, or pentachlorophenol.

It is believed that the selected organic solvent stabilizes the enzyme in liquid media by protecting the functional group site, that is the part of the molecule where the substrate reaction actually occurs or is catalyzed and by protecting the enzyme from microbial contamination and thus degradation. There is obviously some physical or chemical reaction occurring in the concentrated solvent media since the enzyme has no catalytic activity for the substrate at this solvent concentration. However on dilution the enzyme is restored to full activity and maintains its full reactivity at high levels over extended storage periods of from a few months to several years. The internal chemical structure of the enzyme molecule need not be preserved. As long as the reactive site is preserved, the catalytic activity of the enzyme remains intact.

Microbial degradation can also be controlled by use of high sale concentrations such as at least 1% typically 2 to 8 weight % or higher concentration of salts. The salt molecules may also protect the active sites by forming electrostatic bonds protecting the spacial configuration of the enzyme and the active sites.

These and many other objects and attendant advantages of the invention will become apparent as the invention becomes better understood by reference to the following detailed description.

DESCRIPTION OF THE PREFERRED EMBODIMENTS

Enzymes are large molecular weight, complex protein molecules, usually of unknown chemical structure. They are presently classified by their catalytic activity and extreme substrate specificity. Enzymes may be redefined as biological catalysts, capable of catalyzing a reaction of a single substrate, or a reaction of a similar group of substrates.

Typical enzymes are lactate dehydrogenase (LDH) and malate dehydrogenase (MDH) and the like. The enzyme is present in the diluted, stabilized composition in an amount typically from 100 I.U. to 10,000 I.U.

Substrates are organic chemicals of known structure, whose reactions or interactions are catalyzed by enzymes resulting in a change in the compound's structure, atomic composition, or stereo-chemical rotation.

In general substrates are prone to microbiological degradation as they serve as food for bacteria, fungi, and other microorganisms. Otherwise, these compounds remain stable in aqueous media at or near neutral pH (i.e. pH range of 4–10).

Typical substrates are L-alanine, pyruvate, L-aspartate, alpha-ketoglutarate, and the like. The substrates are usually in salt form and form part of the salt concentration useful in enhancing stability of the enzyme. The enzymatic stability increases with substrate concentration. However at high substrate concentrations over about 8% enzymatic activity is inhibited. Therefore the substrate concentration should be optimized, generally at about 2 to 4%.

The buffer salt also provides part of the salt concentration discussed above. The buffer salt is added in an amount necessary to maintain pH between 4–10, typically from 6–8. Generally the buffer is a combination of 0.1–1% of an alkali metal hydroxide and 0.5 to 3% of an alkali metal acid carbonate or phosphate. The total salt concent also effects the amount of polymer required. At higher salt content, e.g. above 4% by weight, less polymer is required due to the electrostatic stabilization provided by the salt. However, at higher salt content, the polymer may cloud the solution or precipitate requiring warming the solution to redissolve.

The polymer is preferably provided in the diluted stabilized solution up to an amount that remains in homogenous suspension under refrigeraton without precipitation. The polymer is present in an amount from 0.01 to 0.5% preferably from 0.05 to 0.25%. Water soluble polymers useful as stabilizing agents in this invention are those that do not inhibit enzymatic activity, and are capable of entrapping the enzyme in the polymer matrix. The polymer may be a synthetic organic material such as polyvinylpyrrolidine or dextran of biologic origin such as gelatin which is denatured collagen.

The solvent must be miscible with water, of neutral or alkaline pH, liquid at room and refrigerator temperatures, and non-degradatively reactive with reactive sites of the enzyme other than formation of electrostatic bonds. Useful solvents are generally polar organic solvents such as ethers, ketones, sulfones, sulfoxides and alcohols such as methanol, ethanol, propanol, butanol, acetone, dioxane, DMSO, dimethylsulfone and THF. However, higher activity at lower solvent concentration for the treatment step is found for liquid polyol solvents containing from 2–4OH groups and containing from 2–10 carbon atoms such as glycerol, propanediol, butane diol, ethylene glycol and the like.

The solvent must be present in an amount of at least 20% during the treatment step typically from 25 to 50%. Some solvents require concentrations as high as 70% in order to maintain stabilized activity above 60% enzymatic reactivity. In the diluted stabilized solution, the solvent is present in an amount of 0.5% to 5%.

Specific examples of practice follow:

EXAMPLE 1

| Enzyme Base | |
|---|---|
| Material | Amount |
| Gelatin | 0.1% W/W |
| 1,2 propane diol | 30% V/V |
| Water | 70% V/V |

Ammonium sulfate suspension (2.2 M) or dry lyophilized LDH enzyme in an amount equivalent to 22,500 IU/l was dissolved in the enzyme base and held at 4°–30° C. for 2–3 days.

| Substrate Reagent | |
|---|---|
| Material | Amount |
| L-Alanine | 22 g/l |
| Alpha-ketoglutaric acid | 1.6 |
| $KH_2PO_4$ | 14 |
| NaOH | 5 |
| $NaN_2$ | 1 |
| Gelatin | 1 |

The enzyme base was diluted thirty-fold by addition to the substrate reagent suspension and mixed to obtain a homogenous suspension. The suspension is stored refrigerated. Projected shelf life under refrigeration is three years with 50–90% activity remaining.

In the clinical diagnostic field the commercial application of these stabilizing methods is represented by, but not limited to, the diagnostic reagents used to determine and quantitate the following constituents in biological fluids:

1. Glutamic-oxalacetic transaminase (SGOT);
2. Glutamic-pyruvic transaminase (SGPT);
3. Lactic dehydrogenase (LDH-P);
4. Creatine phosphokinase (CPK);
5. α-Hydroxybuterid dehydrogenase (α-HBD)
6. Glucose (via Hexokinase-G-6-PDH).

These reagents react similarily, contain some common labile ingredients, and some of the chemical reactions involved are common. The following chemical reaction scheme is presented as a model to illustrate the general nature of the reactions involved:

REACTION SCHEME 1.—GENERAL MODEL

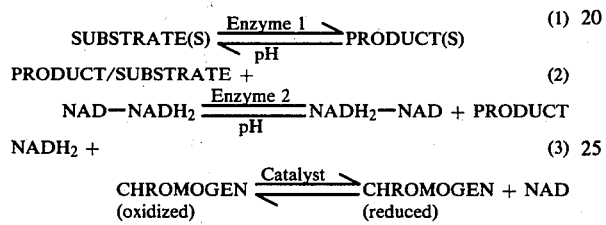

All enzymatic reactions listed above will follow this general scheme, where reaction (2) is usually referred to as the coupling reaction, reactions (2) or (3) are the measuring reactions, and reaction (1) may be characterized as the primary reaction. It is understood however, that not all three reactions are required for measurement; in fact, they may be limited to two, or one. In the case of the ultraviolet measurement of lactic dehydrogenase (LDH) activity, only reaction (2) is involved, as follows:

REACTION SCHEME 2.—LDH

Conversely, more than the three reactions listed may be involved as in the case of Creatine phosphokinase (CPK):

REACTION SCHEME 3.—CPK

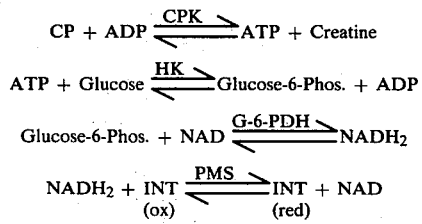

SYMBOLS:
CP = Creatine phosphate
ADP = Adenosine-5'-diphosphate
ATP = Adenosine triphosphate
HK = Hexokinase
NAD = nicotinamide-adenine dinucleotide
$NADH_2$ = nicotinamide-adenine dinucleotide, reduced
G-6-PDH = Glucose-6-phosphate dehydrogenase
INT = tetrazolium salt
PMS = phenazine methosulfate.

In this case, reactions (2) and (3) may be considered the coupling reactions, reactions (3) or (4) the measuring reactions, and reaction (1) the primary reaction.

Referring to REACTION SCHEME 1,—GENERAL MODEL, it becomes obvious and is general knowledge that the use of the reaction sequence permits the analytical quantitation of either the reacting substrates/products or the catalyzing enzymes.

The quantitation of these constituents in biological fluids is a well accepted and widely used diagnostic tool in diagnosis and treatment of human and animal disease states.

It is to be realized that only preferred embodiments of the invention have been described and that numerous substitutions, modifications and alterations are permissible without departing from the spirit and scope of the invention as defined in the following claims.

What is claimed is:

1. A method of stabilizing a labile enzyme used in biological diagnostic determinations and which is unstable in an aqueous media, said method comprising the steps of:
   forming a solution of the enzyme molecule selected from the class consisting of malate dehydrogenase and lactate dehydrogenase in an aqueous media containing 20% to 40% of 1,2-propanediol, at least 0.05% by weight of water-soluble gelatin polymer, and salt including a substrate and a buffer, and a bactericidal agent which inhibits deterioration of said enzyme;
   maintaining the enzyme in said solution for a time sufficient to stabilize reactive sites thereof;
   diluting the solution with water to an enzyme content of at least 100 I.U., solvent content between 0.05% and 5%, a water-soluble polymer content of 0.05% to 0.5%, a salt content of 1% to 8%; and the bactericidal agent content from 0.01% to 0.03%
   and storing the diluted composition at refrigerator temperatures for a period over one month without significant loss of enzymatic activity.

2. A method of stabilizing a labile enzyme used in biological diagnostic determinations of glutamic oxalacetic transaminase (SGOT) and glutamic-pyruvic transaminase (SGPT), and which enzyme is unstable in an aqueous media, and which enzyme is primarily effective in affecting the reactivity of SGOT or SGPT to render a determination of the SGOT or SGPT, said method comprising the steps of:
   forming a solution of an enzyme molecule in an aqueous media containing at least 20% of non-reactive water-miscible, organic solvent which is liquid at room temperature, at least 0.05% by weight of water-soluble polymer, and a bactericidal agent which inhibits deterioration of said enzyme, said enzyme being selected from the class consisting of malate dehydrogenase (MDG) and lactate dehydrogenase (LDH);
   maintaining the enzyme in said solution for a time sufficient to stabilize reactive sites thereof; and
   diluting the solution with water to an enzyme content of at least 100 I.U., a solvent content of no more than 5% and a water-soluble polymer content of at least 0.01% and which solvent content does not materially affect any reaction between the enzyme and SGOT or SGPT when present in such limited amount.

3. A method according to claim 2 in which the solvent is a liquid polyol containing from 2−10 carbon atoms and 2−4 hydroxyl groups said solvent being present in the final composition in an amount from 0.05% to about 5.0%, the bactericidal agent is present in an amount from a 0.01% to about 0.3%, and said polymer is a protein polymer present in an amount from 0.05% to about 0.5%.

4. The method of claim 2 further characterized in that said solvent is present after dilution in an amount from 0.05% to about 5%, said polymer is present after dilution in an amount from 0.05% to about 0.5%, and said bactericidal agent is present after dilution in an amount from 0.01% to about 0.3%.

5. The method of claim 2 in that said composition does not require further substantial dilution for use in biological diagnostic determinations.

6. A method according to claim 2 further including the step of storing the diluted composition at refrigerator temperature for a period over one month without significant loss of enzymatic activity.

7. A method according to claim 2 in which the solvent is an organic solvent selected from ketones, ethers, sulfones, sulfoxides and alcohols.

8. A method according to claim 7 in which the solvent is a liquid polyol containing from 2-10 carbon atoms and 2-4 hydroxyl groups.

9. A method according to claim 8 in which the solvent is 1,2-propanediol present in the treatment step in an amount from 20 to 40%.

10. A method according to claim 2 in which the polymer is gelatin present in said solution in an amount from 0.05 to 0.5%.

11. A method according to claim 10 in which the diluted solution contains 1 to 8% salts including substrate and buffer and from 0.01 to 0.3% of said bactericidal agent.

12. A method of stabilizing a labile enzyme used in biological diagnostic determinations and which is unstable in an aqueous media, and which enzyme is primarily effective in affecting the reactivity of one or more biological constituents to render a determination of such constituent or constituents, said method comprising the steps of:
forming a solution of the enzyme molecule in an aqueous media containing at least 20% of non-reactive water-miscible, organic solvent which is liquid at room temperature, at least 0.05% by weight of water soluble polymer, and a bactericidal agent which inhibits deterioration of said enzyme;
maintaining the enzyme in said solution for a time sufficient to stabilize reactive sites thereof;
diluting the solution with water to an enzyme content of at least 100 I.U., a solvent content of no more than 5% and a water-soluble polymer content of at least 0.01% and which solvent content does not materially affect any reaction between the enzyme or the biological constituent or constituents when present in such amount, said composition not requiring further substantial dilution for use in biological diagnostic determinations.

13. A method according to claim 12 in which the solvent is a liquid polyol containing from 2-10 carbon atoms and 2-4 hydroxyl groups, said solvent being present in the final composition in an amount from 0.05% to about 5.0%, the bactericidal agent is present in an amount from a 0.01% to about 0.3%, and said polymer is a protein polymer present in an amount from 0.05% to about 0.5%.

14. The method of claim 12 further characterized in that said solvent is present after dilution in an amount from about 0.05% to about 5%, said polymer is present after dilution in an amount from 0.05% to about 0.5%, and said bactericidal agent is present after dilution in an amount from 0.01% to about 0.3%.

15. The method of claim 12 in that said enzyme is selected from the class consisting of malate dehydrogenase and lactate dehydrogenase.

16. The method of claim 12 in that the biological diagnostic determination is made with biological constituents selected from the class consisting of glutamic-oxalacetic transaminase (SGOT) and glutamic-pyruvic transaminase (SGPT).

17. A method according to claim 12 further including the step of storing the diluted composition at refrigerator temperature for a period over one month without significant loss of enzymatic activity.

18. A method according to claim 12 in which the solvent is an organic solvent selected from ketones, ethers, sulfones, sulfoxides and alcohols.

19. A method according to claim 18 in which the solvent is a liquid polyol containing from 2-10 carbon atoms and 2-4 hydroxyl groups.

20. A method according to claim 19 in which the solvent is 1,2-propanediol present in the treatment step in an amount from 20 to 40%.

21. A method according to claim 12 in which the polymer is gelatin present in said solution in an amount from 0.05 to 0.5%.

22. A method according to claim 21 in which the diluted solution contains 1 to 8% of salts including substrate and buffer and from 0.01 to 0.3% of said bactericidal agent.

23. A method according to claim 22 in which the bacteriacidal agent is present in said solution in an amount from 0.01 to 0.3%.

24. A method according to claim 20 in which the bacteriacidal agent is selected from the class consisting of sodium azide, benzoic acid, phenol, thymol and pentachlorophenol.

25. A method according to claim 24 in which the biological constituent to be determined is selected from the class consisting of hexokinase, creatine phosphokinase, lactic dehydrogenase (LDH-P), glutamic-pyruvic transaminase, glutamic-oxalacetic transaminase, and a-hydroxybuteric dehydrogenase.

26. A method according to claim 25 in which the enzyme is selected from the class consisting of lactic dehydrogenase and malate dehydrogenase.

* * * * *